US006832109B2

United States Patent
Nissilä

(10) Patent No.: US 6,832,109 B2
(45) Date of Patent: Dec. 14, 2004

(54) WRIST-WORN DEVICE FOR DISPLAYING AND SETTING HEART RATE PARAMETERS

(75) Inventor: Seppo Nissilä, Oulu (FI)

(73) Assignee: Polar Electro Oy, Kempele (FI)

(*) Notice: Subject to any disclaimer, the term of this patent is extended or adjusted under 35 U.S.C. 154(b) by 457 days.

(21) Appl. No.: 09/969,755

(22) Filed: Oct. 3, 2001

(65) Prior Publication Data

US 2002/0052556 A1 May 2, 2002

(30) Foreign Application Priority Data

Oct. 6, 2000 (FI) ............................................ 20002210

(51) Int. Cl.[7] ............................................. A61B 5/0402
(52) U.S. Cl. ..................................................... 600/509
(58) Field of Search ........................... 362/23, 84, 103; 482/8, 9; 600/500–503, 509, 520, 519; 607/2

(56) References Cited

U.S. PATENT DOCUMENTS

| 4,151,707 | A | * | 5/1979 | Cobelli | 368/190 |
| 4,186,489 | A | * | 2/1980 | Vigilante et al. | 33/2 H |
| 4,843,720 | A | | 7/1989 | Kim | |
| 5,214,624 | A | | 5/1993 | Siebrasse | |
| 5,579,777 | A | * | 12/1996 | Suga | 600/500 |
| 5,732,475 | A | * | 3/1998 | Sacks et al. | 33/555.4 |
| 5,769,755 | A | | 6/1998 | Henry et al. | |
| 5,980,060 | A | | 11/1999 | Chien | |

FOREIGN PATENT DOCUMENTS

| CH | 276 769 | 10/1951 |
| EP | 0 165 505 A1 | 12/1985 |
| GB | 2 247 838 | 3/1992 |
| GB | 2 284 156 A | 5/1995 |
| GB | 2 383 416 A | 6/2003 |
| JP | 58 195540 | 11/1983 |
| WO | WO 00/50963 | 8/2000 |

OTHER PUBLICATIONS

Patent Abstracts of Japan, vol. 017, No. 685, Dec. 15, 1993.

* cited by examiner

*Primary Examiner*—Jeffrey R. Jastrzab
*Assistant Examiner*—Frances P Oropeza
(74) *Attorney, Agent, or Firm*—Hoffmann & Baron, LLP

(57) ABSTRACT

A wrist-worn device comprising a display for showing a heart rate parameter value, such as a heart rate measured from a person's body or a heart rate variable derived from the heart rate. The display comprises at least two display areas which display areas the wrist-worn device is arranged to employ to show that a heart rate parameter momentarily belongs to a heart rate parameter value range corresponding to the display area and which wrist-worn device comprises at least one sliding means for selecting a desired heart rate parameter value range by mechanically sliding the sliding means to cover at least one display area at a time.

15 Claims, 2 Drawing Sheets

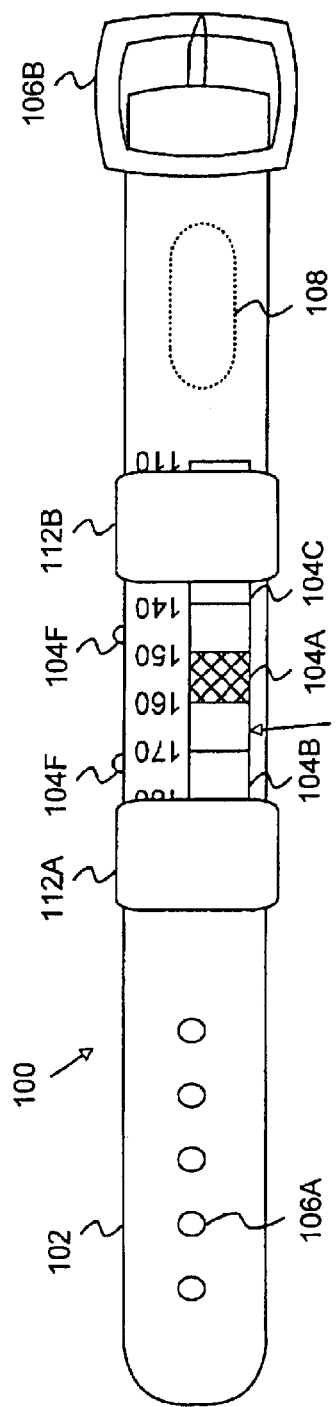
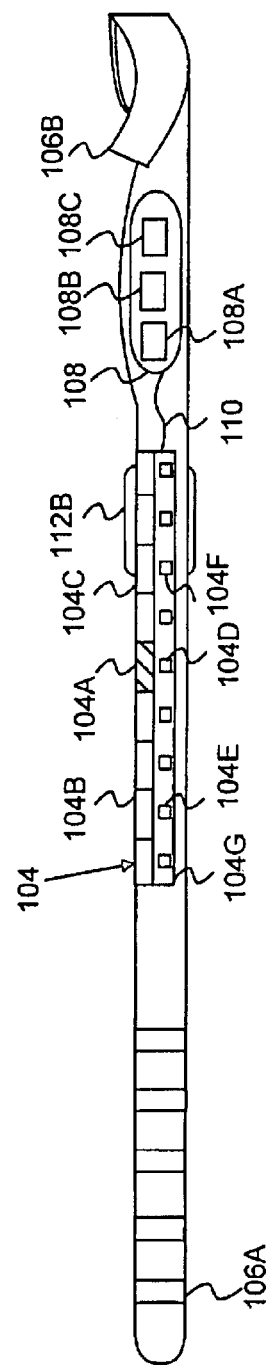
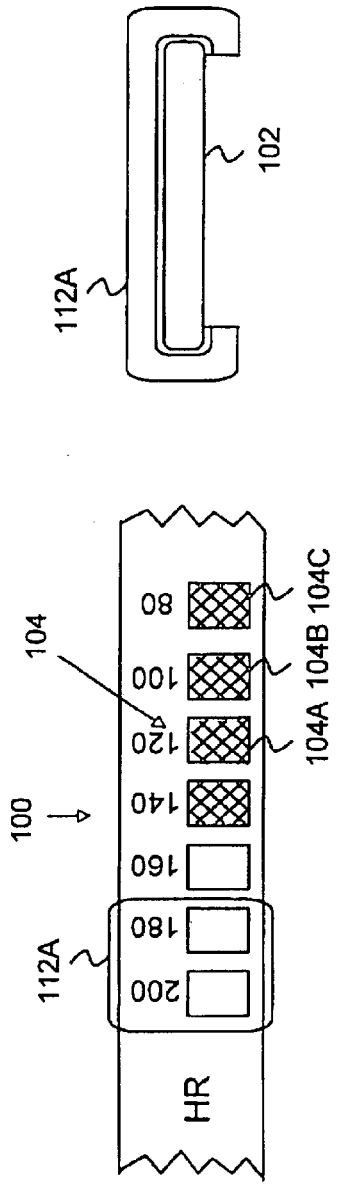
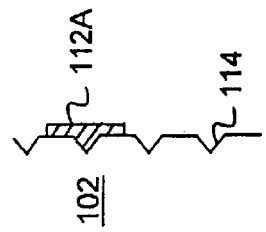

WRIST-WORN DEVICE FOR DISPLAYING AND SETTING HEART RATE PARAMETERS

FIELD OF THE INVENTION

The field of application of the invention comprises wrist-worn devices, such as heart rate monitors, wrist-worn computers, or the like. The invention particularly relates to the setting of user-specific heart rate parameter limits in a wrist-worn device.

BACKGROUND OF THE INVENTION

The evaluation and planning of the intensity of an exercise is important both to a fitness enthusiast as well as a competing athlete. A reliable method for evaluating the intensity is to monitor the frequency of heartbeat, i.e. heart rate, measured from the person's body. Depending on the target intensity set for the exercise, the user may try to maintain the heart rate within a desired range. For example, in a fat-burning exercise of a long duration, the aim may be to keep the heart rate between 100 and 120 beats per minute, whereas a competing athlete engaged in a high-tempo interval training may aim for example at momentarily raising the heart rate level to 160–180 and then again lowering it to 120–140.

Heart rate is measured from the body using a heart rate monitor. The measurement may be carried out in various ways, for example from electric signals caused by heartbeat to the chest, from a pressure pulse caused by blood on the wrist, or optically from the circulation of blood in the wrist. A common embodiment of a heart rate monitor comprises a transmitter electrode belt to be placed on the chest to transmit measured heart rate information to a receiver unit carried on the wrist, the receiver unit displaying the information to the user. The wrist-worn receiver usually comprises, in addition to a liquid crystal display, keys for the user to input data and sound signalling means. With the keys, the heart rate limits within which the user wishes his heart rate to remain during the exercise are supplied to the heart rate monitor. If the user's heart rate does not remain within the set limits, the monitor produces a sound signal to allow the user to check his momentary heart rate on the display and to adjust the exercise intensity accordingly.

The prior art solutions for monitoring heart rate limits are not convenient to use. A heart rate value is difficult to read from a liquid crystal display, particularly in the dark. The setting of heart rate limits with the keys is often complicated, difficult and slow.

BRIEF DESCRIPTION OF THE INVENTION

It is an object of the invention to provide an improved solution for setting heart rate parameter limits in a wrist-worn device. This is achieved with a wrist-worn device comprising a display for showing a heart rate parameter value, such as a heart rate measured from a person's body or a heart rate variable derived from the heart rate. The display comprises at least two display areas which display areas the wrist-worn device is arranged to employ to show that a heart rate parameter momentarily belongs to a heart rate parameter value range corresponding to the display area and which wrist-worn device comprises at least one sliding means for selecting a desired heart rate parameter value range by mechanically sliding the sliding means to cover at least one display area at a time.

The preferred embodiments of the invention are disclosed in the dependent claims.

The invention thus relates to a novel solution for setting heart rate parameter limits in a wrist-worn device. In this specification of the invention, the term wrist-worn device refers to equipment comprising heart rate measurement functions and the displaying of a measured heart rate or a heart rate variable derived from the heart rate. Heart rate monitors and wrist-worn computers provided with a heart rate measuring function are thus examples of equipment the invention relates to. The heart rate parameters to be displayed for which the limits are to be set include heart rate, average heart rate or rate deviation.

In this context, the term display refers to the parts of the device used for visually displaying an exercise variable value to the user. In a preferred embodiment of the invention, the display is composed of separate display areas. The display is preferably formed on a resilient and flexible circuit board, and each display area corresponding to a specific exercise variable value can be illuminated with a display-area-specific illumination element, such as a LED (Light Emitting Diode). The illumination elements, or light sources, do not necessarily have to be close together, but they may be arranged on various locations on the wristband. The number of the display areas used for displaying the exercise variable values is naturally not limited in invention either. In a preferred embodiment, the topmost layer of the display is made of a translucent plastic to make the light emitted by a display-area-specific light source visible to the user. The light sources may also be placed on the surface of the wrist-worn device, uncoated by the plastic encapsulating the device. The display is preferably a bar display comprising a string of display areas arranged along a substantially straight line with respect to each other in the longitudinal direction of the wristband. A first end of the bar display thus comprises a value range corresponding to the lowest exercise variable values that can be displayed, a second end comprising in turn a value range corresponding to the highest exercise variable values that can be displayed. An exercise variable value can be displayed for example by only illuminating the display area to which the exercise variable value relates. Alternatively, all value ranges lower than said value range are illuminated, in addition to the value range concerned. Instead of a bar display, a display forming an arc can also be used.

The wrist-worn device preferably comprises an electronics unit, which receives the heart rate information from a heart rate transmitter or from the electrodes of the wrist-worn device. The wristband, the display and the electronics unit are preferably integrated to form a single entity, i.e. a uniform piece. Integration as used in this context means that the parts of the device are joined together process-technically during the manufacturing phase, for example by injection moulding, in which the parts are coated with plastic to produce a uniform piece. The parts thus form a wrist-worn device in which the display and the electronics unit can be thought of as integral parts of the wristband with which the device can be attached to the wrist. With injection moulding, the wrist-worn device can be manufactured in a plural number of phases, whereby different plastics with different transparency and colour properties can be used. For example, the part of the wrist-worn device that encapsulates the display is made using transparent plastic.

The heart rate limits are set using mechanical sliding means, i.e. a piece which at least partly surrounds the wristband or the display area and can be slid on the wristband. The sliding means is meant to cover a portion of the display, for example the display areas of the display forming a bar-shaped arrangement which correspond to unwanted heart rate parameter value ranges. If the display areas are in a ring-shaped formation on the wrist-worn device, the device is provided for example with slide protrusions on the surface, on both sides of the display areas, the protrusions allowing the sliding means to be slid on the display areas. In a ring-shaped arrangement, the display areas form a part of a sector, for example, the sliding means being preferably of a corresponding formation. It is apparent that the above solution of slide protrusions can also be applied to a bar display. To ensure that the sliding means stays in place on the desired location on the wristband, it preferably comprises a slot or a toothing that can be engaged with counter pieces provided on the wristband to secure the sliding means in place. The wrist-worn device preferably comprises two sliding means, an upper sliding means for covering an area above the desired heart rate parameter area, and a lower sliding means for covering an area below the desired heart rate parameter area. The user thus aims at keeping the heart rate parameter value, such as heart rate, between the sliding means during the exercise. In a preferred embodiment of the invention, the sliding means are transparent, the light emitted by the light source of the bar display being at least partly visible through the sliding means. In a preferred embodiment of the invention, the sliding means are made in different colours corresponding to the area covered by the sliding means; for example, the upper sliding means may be red and lower sliding means yellow. Alternatively, the heart rate parameter value may be controlled with a wrist-worn device having a single sliding means, which may be green, for example. The sliding means is placed on top of the allowed heart rate area, the transparent sliding means thus allowing the user to control that the heart rate parameter value remains on the display areas covered by the sliding means, i.e. within the desired value range.

An advantage of the invention is that it provides an improved wrist-worn device solution in which the setting of heart rate limits is quick and simple. The solution offers to the user a concrete means for monitoring that the heart rate parameter value remains within the desired value range.

BRIEF DESCRIPTION OF THE INVENTION

In the following, the invention will be described in greater detail with reference to the accompanying drawings, in which FIG. 1 shows a top view of an embodiment of a wrist-worn device;

FIG. 2 shows a sectional side view of a preferred embodiment of the wrist-worn device;

FIG. 3A shows an embodiment of a display and a sliding means;

FIG. 3B shows an embodiment of the wrist-worn device and a sliding means attached to it;

FIG. 3C shows an embodiment of means for arranging the sliding means in place with respect to the wrist-worn device.

DESCRIPTION OF EMBODIMENTS

Figure 4:
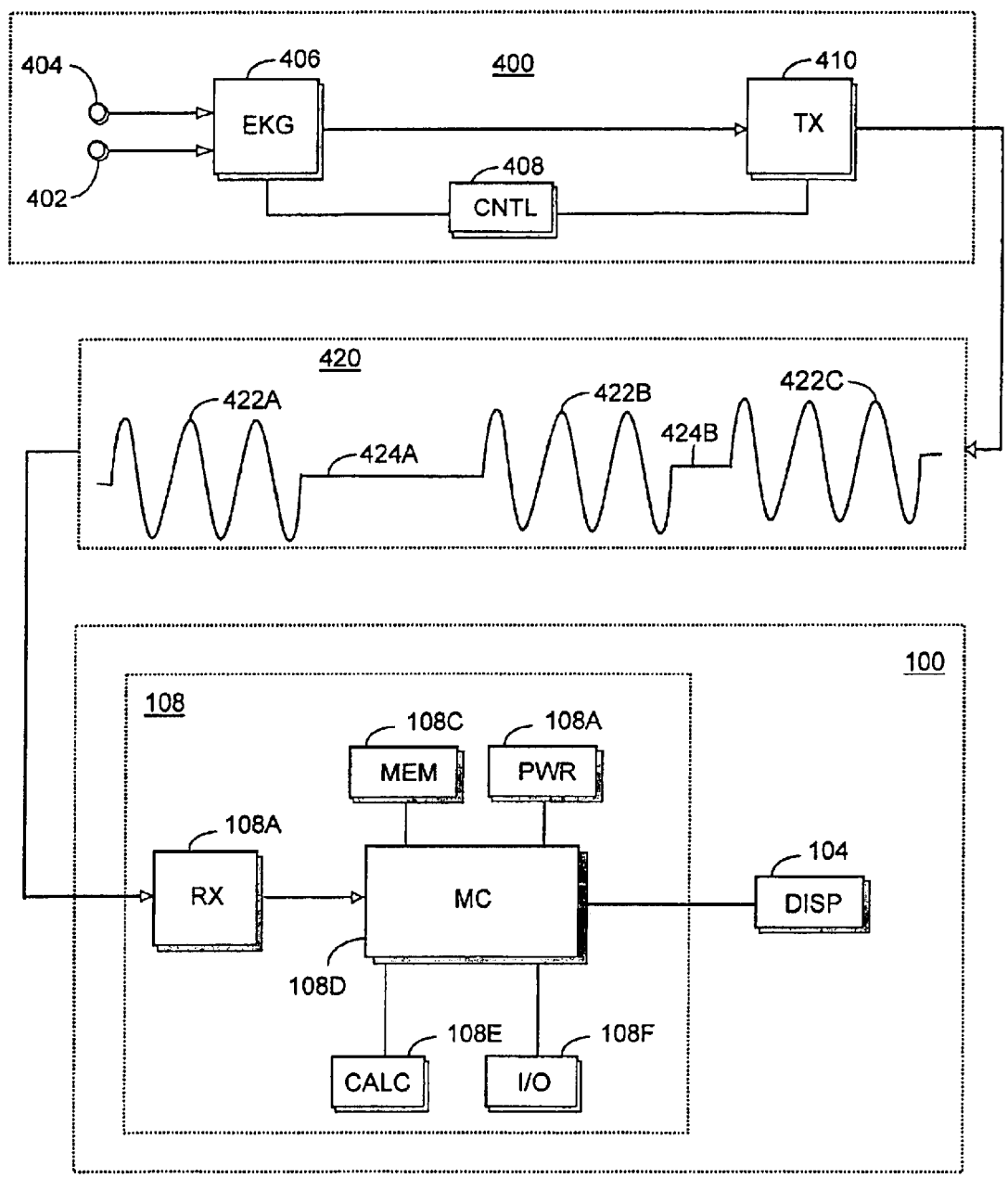
FIG. 4 illustrates embodiments of a heart rate transmitter and the wrist-worn device.

In the following, the invention will be described with reference to preferred embodiments and the accompanying FIGS. 1–4. FIG. 1 shows a wrist-worn device 100 according to a preferred embodiment of the invention. The wrist-worn device 100 comprises a wristband 102 and a display 104 showing a momentary value of heart rate used as an exercise variable. The display is divided into display areas of ten heartbeats, such as areas of 140–150 and 150–160 heartbeats per minute. In the example of FIG. 1, the momentary exercise variable value, i.e. heart rate, is shown on a display area 104A. In other words, the display area 104A is illuminated to show the user that his heart rate is between 150 and 160. Although in FIG. 1 the display is divided into areas of ten heartbeats, the display may be divided into display areas in various other ways as well, for example into areas of five heartbeats.

The wrist-worn device 100 comprises mechanically slidable sliding means 112A and 112B for setting heart rate limits. The sliding means 112A is an upper sliding means covering a heart rate range to which the heart rate should not rise during the exercise, and the sliding means 112B in turn is a lower sliding means covering a heart rate range to which the heart rate should not drop during the exercise. In FIG. 1 the user has wanted to set the optimal heart rate range at 140–180. The Figure also shows that the sliding means 112A is arranged to cover precisely the display areas above the display area 104B, while the lower sliding means 104C only covers half of the display area 104C, i.e. it allows the user to see if the heart rate is in the non-allowed range, but in the immediate vicinity of the allowed area. With a slight increase in the level of intensity the user can thus reach the allowed optimal area again. In FIG. 1 the sliding means 112A–112B are non-transparent, but they could also be made of transparent plastic, for example, to allow the user to see through the sliding means if his heart rate is too high or low with respect to the desired heart rate area. The sliding means 112A–112B of a preferred embodiment are different in colour, the upper sliding means being red and the lower sliding means yellow, any deviation from the desired heart rate area being thus easy to detect on the basis of the colour. The wrist-worn device 100 further comprises attaching means, i.e. holes 106A and 106B, for attaching the device to the wrist. Instead of a buckle attachment, the wrist-worn device may be attached to the wrist using Velcro, for example, or some other known means. The functions of the wrist-worn device 100 are controlled with input keys 104F which are implemented for example as push-buttons, turn-buttons or membrane keys. The wrist-worn device 100 further comprises an electronics unit 108 which is integrated into the device 100 and therefore shown with a broken line in FIG. 1.

FIG. 2 shows a sectional side view of the wrist-worn device 100 of FIG. 1. The display 104 is divided into display areas of which the Figure shows display areas 104A–104C. In the Figure, the display area 104A is activated, i.e. it is momentarily illuminated, with a light source 104D. When necessary, the display area 104B is illuminated with a light source, such as a LED 104E, and the display area 104C with a light source 104F. The light sources 104D–104E are arranged onto a flexible circuit board 104G which forms the base of the display. Because of the circuit board 104G, the display 104 is flexible and bends at least partly around the user's wrist when the device 100 is worn on the wrist. The advantage of this is that the display is not limited solely to a rigid display unit visible on the top side of the wrist, i.e. the side facing away from the palm side of the hand. When built on a flexible circuit board, the display of the wrist-worn device can be extended so as to be visible also on the sides of the wrist and, at least partly, even on the palm side of the hand. The sliding means are represented in FIG. 2 by the lower sliding means 112B which in a preferred embodiment extends at least partly above the top surface level of the wrist-worn device and below its bottom surface level.

With a further reference to FIG. 2, the electronics unit 108 comprises a power source 108A, such as a battery, for producing the current needed by the electronics unit 108 and the display 104. At the bottom of the wrist-worn device 100, for example, there is provided an opening for the battery 108A through which opening the battery can be changed when necessary. The electronics unit 108 further comprises means for receiving heart rate information 108B and means for forming a heart rate 108C on the basis of the heart rate information for display on a display 104B of the wrist-worn device. For the transfer of electric current and information, the display 104 of the device 100 and the electronics unit 108 are interconnected via a connecting line 110 or the flexible circuit board 104G, for example. The user interface is a menu-type hierarchical system, for example, in which push-buttons 104F are used for making selections and for activating and stopping functions, such as a heart rate measurement.

FIG. 2 shows the structure of the wrist-worn device 100 in which the display 104, wire 110 and electronics unit 108 are encapsulated in the wristband 102. The display 104 and the electronics unit 108 are sealed into the wristband 102, i.e. there are no open seams in the solution of the invention between the wristband and said components. This enhances the waterproofness of the device because components sensitive to water are entirely surrounded by plastic. The components are encapsulated to form a uniform piece by injection moulding, for example, which is a technique in which molten plastic mass is injected into a mold and cooled to produce a durable, flexible, sealed and uniform wrist-worn device. At least at the display 104 the plastic cover encapsulating the wrist-worn device 100 is made of transparent plastic to allow the display 104 to be made visible. An injection moulding process in which different plastics and colours are used is technically possible by encapsulating the wrist-worn device in several stages and changing the plastic between the stages. Although in FIG. 2 the top surface/exterior face of the display 104 is level with the top surface of the device 100, the solution of the invention is not restricted to this, but the wrist-worn device 100 may also be implemented such that half of the display 104 is inside the area defined by the wristband, the display 104 thus partly rising above the level of the wristband 102. If the display is partly above the surface of the wrist-worn device, the one or more sliding means are correspondingly raised to allow them to be moved over the display also in this case.

FIG. 3 illustrates another example of showing exercise variable information on a bar display of the wrist-worn device. In this example, the display areas 104A and 104B on the display of the device 100A are not arranged to be in immediate contact with each other, but separated by the plastic in which the device 100A is encapsulated. When the display areas 104A and 104B are activated, they are thus shown as separate luminous points on the device 100. In the wrist-worn device of FIG. 3, the display area 104A indicating a momentary value and all display areas 104B–104C indicating values lower than the momentary value are illuminated. The device 100 of FIG. 3 comprises one sliding means, i.e. the upper sliding means, which is in this example at least partly transparent or translucent and thereby allows light emitted by the light sources covered by the sliding means to be seen by the user, when necessary. The displays shown in FIGS. 1–3 are all bar-type displays in which at least some of the display areas are substantially on a straight line with respect to each other. The display formed by the display areas may also be other than bar-shaped; for example, they may form a full circle or a half-circle.

FIG. 3B shows the location of the sliding means 112A with respect to the wristband 102. As shown in the Figure, the sliding means 112A and the wristband 102 are close to each other, preferably in contact with each other. The sliding means 112A at least partly surrounds the top and bottom surfaces and the sides of the wristband 102. The sliding means 112A is secured with regard to the wrist-worn device for example by means of teeth provided in the sliding means 112A and recesses provided in the wristband 102, whereby when a tooth is placed into a recess, the sliding means sets into place. This is illustrated in FIG. 3C which is a view seen from the underside of the wristband 102. The sliding means can be slid along the surface of the wristband, the sliding means 112A being provided with a toothing which can be placed into the recesses of the wristband 102 to secure the sliding means in place. In FIG. 3C the toothing is only provided on one side of the wristband 102, but it is apparent that it may appear on both sides of the devices.

FIG. 4 is a block diagram illustrating the structure of a heart rate transmitter-receiver pair. The Figure only shows the essential parts of the heart rate transmitter, such as an electrode belt 400 to be placed on the chest, and a wrist-worn receiver 100, although a person skilled in the art will find it apparent that other parts may also be included but it is not relevant to describe them in this context. The electrode belt 400 comprises an electronics unit 408 which receives the heart rate information from measurement electrodes 402, 404, which in turn produce an EKG signal measurement by measuring the difference in potential between the electrodes 402–404. The EKG signals are preferably processed, i.e. filtered, amplified and detected, in an EKG detection block 406 using prior art methods to allow heartbeats to be detected from the signal. The detection of heartbeats is based on a QRS complex detected in the heartbeat signal, for example, the letters Q, R and S referring to potential phases caused in an electric signal by an electric activation of the heart. The QRS may be detected in a EKG detection block using a matched filter, for example, whereby a model complex is compared with a measured QRS complex and when the comparison exceeds a predetermined threshold value, the complex is accepted as a heartbeat. Heart rate information 420 is transmitted from the electrode belt 400 to the wrist-worn device 100 using the transmitter 410, which is implemented as a coil, for example.

In the heart rate information 420 to be transmitted, one heartbeat or heart rate data bit is represented for example by one 5 kHz burst 422A or a group 422A, 422B, 422C of several bursts. Intervals 424A, 424B between the bursts may be of an equal duration, or their duration may vary. The heart rate information 420 to be transmitted may consist of heartbeat information, as described above, or the heartbeats may be used already in the transmitter 400 to form computational exercise variables, such as an average heart rate or heart rate deviation. The computational variables can naturally also be formed in the wrist-worn device 100, on the basis of the heart rate information. The information 420 may be transmitted inductively, or it may be sent optically or through a wire. The wrist-worn device 100 and its electronics unit 108 in particular comprise receiver means 108B, such as a coil. A signal received with the receiver means 108B is supplied to control electronics 108D which control and coordinate the operation of the electronic parts of the wrist-worn device 100. The control electronics 108D together with the related memory are preferably implemented using a general-purpose microprocessor provided with the necessary system and application software, although diverse hardware implementations are also possible, such as a circuit built of separate logic components, or one or more ASICs (Application Specific Integrated Circuit).

The wrist-worn device 100 comprises electric current produced for the electronics unit 108 and the display by a power source 108A. The device 100 preferably comprises a memory 108C for storing the received heart rate information 420 and the computer software of the device 100. The received heart rate information 420 is processed in a computation unit 108E of the electronics unit 108 to produce the user's heart rate and/or other heart rate variables for display on the display 104 connected to the electronics unit 108. The wrist-worn device 100 preferably comprises a user interface 108F for supplying information to the device 100 and for transferring information stored on the device 100 to an external computer, for example, for further processing. Input functions at the user interface 108F are implemented for example using push-buttons and/or membrane keys for making selections and for activating and stopping functions, such as a heart rate measurement. The user interface 108F preferably also comprises means for producing sound signals to indicate when the time reserved for the exercise has elapsed, for example. The user interface 108F, which may also incorporate a telecommunications port, for example, can also be used for updating the software of the wrist-worn device.

Although the heart rate monitor described with reference to FIG. 4 comprises an electrode belt 400 to be placed on the chest and a device 100 to be carried on the wrist, a heart rate monitor composed of a single-piece wrist-worn device 100 is also possible. In that case the device comprises pressure sensors to measure heart rate information from the circulation of blood in a vein. When a single-piece device is concerned, the heart rate information is transmitted from the sensors to the electronics unit using conductive plastic or a connecting wire, for example.

Although the invention is described above with reference to examples according to the accompanying drawings, it is apparent that the invention is not restricted to them, but may vary in many ways within the inventive idea disclosed in the claims.

What is claimed is:

1. A wrist-worn device comprising:
   a display for showing a heart rate parameter value, said display having at least two display areas arranged to show a measured heart rate parameter, each display area representing a heart rate parameter value range; and
   at least one sliding means mechanically engageable with said display for selecting a desired heart rate parameter value range by mechanically sliding the sliding means to cover at least one display area at a time.

2. A wrist-worn device according to claim 1, wherein the sliding means is adapted to cover at least one display area representing a heart rate parameter value range where the heart rate parameter value should not be.

3. A wrist-worn device according to claim 1, wherein the display is a bar display composed of a string of display areas in a bar-shaped arrangement.

4. A wrist-worn device according to claim 1, wherein the display is a ring-shaped display composed of adjacent display areas in a ring-shaped arrangement.

5. A wrist-worn device according to claim 1, wherein the sliding means is adapted to cover at least one display area representing a heart rate parameter value range where the heart rate parameter value should be.

6. A wrist-worn device according to claim 3, wherein the wrist-worn device is arranged to display that a heart rate parameter momentarily belongs to the highest value range of the display area at a first end and that a heart rate parameter belongs to the value range comprising the lowest values of the display area at a second end of the bar display.

7. A wrist-worn device according to claim 1, wherein the sliding means is made of at least partly transparent plastic to allow the display area to be seen through the sliding means.

8. A wrist-worn device according to claim 1, wherein the wrist-worn device comprises an upper sliding means serving as a sliding means to cover at least one display area representing values which a momentary heart rate parameter value should not exceed, the wrist-worn device further comprising a lower sliding means serving as a sliding means to cover at least one display area representing values under which the momentary heart rate parameter value should not drop.

9. A wrist-worn device according to claim 8, wherein the upper sliding means and the lower sliding means are different in colour to allow the user to distinguish between the two sliding means.

10. A wrist-worn device according to claim 1, wherein the wrist-worn device comprises a flexible circuit board, the display being formed on the circuit board to make the device flexible.

11. A wrist-worn device according to claim 1, wherein the display comprises an illumination element for at least one display area to illuminate the display area when a momentary heart rate parameter value is within a heart rate parameter value range corresponding to the display area in question.

12. A wrist-worn device according to claim 1, wherein the wrist-worn device comprises a wristband for attaching the device around the wrist, the wrist-worn device further comprising an electronics unit arranged to process a heart rate parameter value shown on the display, the wristband of the wrist-worn device, the electronics unit and the display being sealably integrated using plastic to form a single, uniform wrist-worn device.

13. A wrist-worn device according to claim 12, wherein the part of the wrist-worn device which encapsulates the display is made of transparent plastic.

14. A wrist-worn device according to claim 12, wherein the electronics unit comprises receiver means for receiving a person's heart rate information and calculation means for processing the heart rate information to form a heart-rate parameter to be shown on the display of the wrist-worn device.

15. A wrist-worn device comprising:
   a display for showing a heart rate parameter value, said display having at least two display areas arranged to show a measured heart rate parameter, each display area representing a heart rate parameter value range; and
   at least one sliding means for selecting a desired heart rate parameter value range by mechanically sliding the sliding means to cover at least one display area at a time, wherein the sliding means comprises a first toothing and the wrist-worn device comprises a second toothing, which first toothing and second toothing can be engaged with each other to secure the sliding means in place on a desired location on top of the display of the wrist-worn device.

* * * * *